United States Patent
Liu et al.

[11] Patent Number: 6,077,849
[45] Date of Patent: Jun. 20, 2000

[54] ANTIDIABETIC AGENTS

[75] Inventors: Kun Liu, Edison; Harold B. Wood, Cranford; Anthony B. Jones, Scotch Plains; Bei Zhang, Edison, all of N.J.

[73] Assignee: Merck & Co., Inc., Rahway, N.J.

[21] Appl. No.: 09/280,602

[22] Filed: Mar. 29, 1999

Related U.S. Application Data

[60] Provisional application No. 60/080,398, Apr. 2, 1998, and provisional application No. 60/096,135, Aug. 10, 1998.

[51] Int. Cl.[7] .......................... A61K 31/47; A61K 31/40; C07D 209/12; C07D 333/56; C07D 317/44

[52] U.S. Cl. .................... 514/307; 514/419; 514/443; 514/469; 546/146; 548/494; 549/58; 549/446

[58] Field of Search .................... 546/146; 514/307, 514/419, 443, 469; 548/494; 549/58, 446

[56] References Cited

U.S. PATENT DOCUMENTS

| | | | |
|---|---|---|---|
| 4,540,704 | 9/1985 | Ueda et al. | 514/389 |
| 5,338,855 | 8/1994 | Yoshioka et al. | 514/369 |
| 5,583,149 | 12/1996 | Cipollina et al. | |
| 5,726,125 | 3/1998 | Phillion et al. | 504/193 |
| 5,852,046 | 12/1998 | Lang et al. | 514/419 |

FOREIGN PATENT DOCUMENTS

WO 96/40115  of 0000  WIPO.

OTHER PUBLICATIONS

Arai, et al., Chem. Pharm. Bull., 1981, 29(4): 961–969.
Arai, et al., Chem. Pharm. Bull., 1981, 29(4): 991–999.
Mocek, et al., J. Antibiotics, 1996, 49(9): 854–859.
Shimizu, et al., Gann, 1982, 73: 642–648.

*Primary Examiner*—Deborah C. Lambkin
*Attorney, Agent, or Firm*—James L. McGinnis; David L. Rose

[57] ABSTRACT

Compounds of formula I:

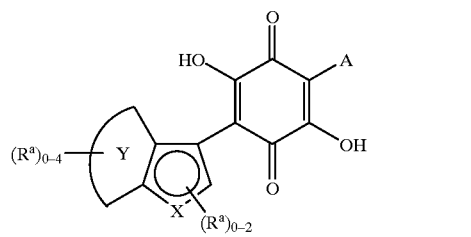

as well as tautomers, pharmaceutically acceptable salts, hydrates, prodrugs and reduced forms are disclosed. The compounds are useful for the treatment and prevention of diabetes mellitus, and in particular, for the treatment or prevention of hyperglycemia in diabetic patients.

24 Claims, No Drawings

ANTIDIABETIC AGENTS

CROSS REFERENCE TO RELATED APPLICATIONS

This application is based on, and claims priority from, provisional applications No. 60/080,398, filed Apr. 2, 1998, and No. 60/096,135, filed Aug. 10, 1998, which are hereby incorporated by reference in their entirety.

BACKGROUND OF THE INVENTION

Insulin is a hormone that is necessary for normal carbohydrate, protein and fat metabolism in mammals. Insulin is known to bind to the extracellular domain (α-subunits) of its specific receptor. Following insulin binding, conformational changes in the insulin receptor lead to autophosphorylation of the intracellular β-subunits and stimulation of the receptor's intrinsic tyrosine kinase activity and activation of insulin signal transduction pathway. The activated insulin receptor tyrosine kinase phosphorylates several intermediate substrates (e.g. IRS-1 and SHC). These proximal events lead to activation of additional signaling intermediates such as PI-3-kinase and MAP kinase. Through an unknown series of additional steps, modulation of key cellular components (e.g. glucose transporter translocation, activation of glycogen synthase, inhibition of gluconeogenic enzymes) coordinate stimulation of glucose disposal and inhibition of hepatic glucose output. Considerable evidence suggests that insulin receptor tyrosine kinase activity is essential for many, if not all of the biological effects of insulin. However, the precise biochemical mechanisms linking receptor kinase-mediated tyrosine phosphorylation to the regulation of cellular metabolic pathways are not completely defined.

Two major forms of diabetes mellitus are now recognized. Type I diabetes, or insulin-dependent diabetes, is the result of an absolute deficiency of insulin, the hormone which regulates glucose utilization, and patients with Type I diabetes are dependent on exogenous insulin for survival. Type II diabetes, or non-insulin-dependent diabetes (NIDDM), often occurs in the face of normal, or even elevated levels of insulin and appears to be the result of the inability of tissues to respond appropriately to insulin (i.e. insulin resistance). Insulin resistance is a major susceptibility trait for NIDDM and is also a contributing factor in atherosclerosis, hypertension, lipid disorders and polycystic ovarian syndrome.

Over time, many individuals with NIDDM show decreased insulin production, which requires supplemental insulin for adequate blood glucose control, especially during times of stress or illness. An exogenous insulin regimen is often required in the treatment of secondary diabetes, i.e., diabetes occurring in relation to other disease states such as pancreatic disease. Insulin is also used in some cases of gestational diabetes to obtain optimum blood glucose control. The conventional route of insulin administration is subcutaneously via a needle and syringe. Continuous subcutaneous insulin infusion with an infusion pump is an alternative to conventional injection therapy for achieving normalized levels of blood glucose.

Conventional treatments for NIDDM, which have not changed substantially in many years, have significant limitations. While physical exercise and a reduction in dietary intake of calories could improve the diabetic condition, compliance with this treatment is generally poor. Increasing the plasma level of insulin by administration of sulfonylureas (e.g. tolbutamide, glipizide) which stimulate the pancreatic β-cells to secrete more insulin, or by injection of insulin after the response to sulfonylureas fails, will result in insulin concentrations that stimulate even highly insulin-resistant tissues. However, dangerously low levels of plasma glucose can result from these last two treatments, and increasing insulin resistance due to the even higher plasma insulin levels could theoretically occur. The biguanides increase insulin sensitivity resulting in some correction of hyperglycemia. However, the two biguanides, phenformin and metformin, can induce lactic acidosis and nausea/diarrhea, respectively.

Thiazolidinediones (glitazones) have been recently described as a class of compounds with a mechanism of action which ameliorates many symptoms of NIDDM. These agents substantially increase insulin sensitivity in muscle, liver and adipose tissue in several NIDDM animal models, resulting in the correction of elevated plasma levels of glucose, triglycerides and nonesterified fatty acids without the occurrence of hypoglycemia. However, undesirable effects associated with the glitazones have occurred in animal and human studies, including cardiac hypertrophy, hemadilution and liver toxicity.

Accordingly, there exists a continuing need for novel therapeutic agents for ameliorating the symptoms of diabetes mellitus, particularly for controlling the blood glucose level in patients, and for the prevention of the onset of diabetes. In addition, there is a need for new therapeutic agents for treating or overcoming insulin resistance in cases where it contributes to the pathogenesis of diseases or disorders.

SUMMARY OF THE INVENTION

The present invention relates to compounds represented by formula I:

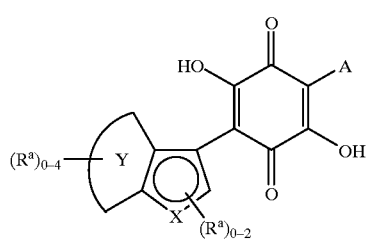

as well as tautomers, pharmaceutically acceptable salts, hydrates, prodrugs and reduced forms thereof wherein:

ring Y represents a 5–6 membered aryl or heteroaryl fused ring, which is optionally substituted with 1–4 groups selected from $R^a$;

X represents O, $S(O)_m$ or N, wherein m is 0, 1 or 2;

A represents a member selected from the group consisting of:
  (a) a 6–10 membered mono- or bicyclic aryl group;
  (b) a 5–6 membered isolated monocyclic heteroaryl group;
  (c) a 9–10 membered bicyclic heteroaryl group, attachment to which is through a 6 membered ring, or
  (d) an 8-membered bicyclic heteroaryl group, the heteroaryl groups having 1–4 heteroatoms selected from O, $S(O)_m$ and N, said aryl and heteroaryl groups being optionally substituted with 1–3 $R^a$ groups;

each $R^a$ is independently selected from the group consisting of:

halo, —OH, —$C_{1-12}$ alkyl$(R^b)_3$, —$C_{2-10}$ alkenyl$(R^b)_3$, —$C_{2-10}$ alkynyl$(R^b)_3$, —$C_{6-10}$ aryl$(R^b)_3$, -heteroaryl $(R^b)_3$, -heterocyclyl$(R^b)_3$, —$NH_2$, —$NHC_{1-6}$ alkyl$(R^b)_3$, —$N(C_{1-6}$ alkyl$(R^b)_3)_2$, —$N_3$, —$OC_{1-6}$ alkyl $(R^b)_3$, —$S(O)_mH$, —$S(O)_mC_{1-6}$ alkyl$(R^b)_3$, —CHO, —$C(O)C_{1-6}$ alkyl$(R^b)_3$, —$CO_2H$, —$C(O)OC_{1-6}$ alkyl$(R^b)_3$, —$C(O)SC_{1-6}$ alkyl$(R^b)_3$, —$C(O)NH_2$, —$C(O)NHC_{1-6}$ alkyl$(R^b)_3$, —$NHC(O)C_{1-6}$ alkyl $(R^b)_3$, —$S(O)_mNH_2$, —$NHS(O)_mC_{1-6}$ alkyl$(R^b)_3$, —$S(O)_mNHC_{1-6}$ alkyl$(R^b)_3$ and —$S(O)_mN(C_{1-6}$ alkyl$(R^b)_3)_2$, and each $R^b$ is independently selected from: H, OH, halo, —$C_{1-4}$ alkyl, —$C_{2-4}$ alkenyl, —$C_{2-4}$ alkynyl, —$CF_3$, —$OCF_3$, —$NO_2$, —$N_3$, —CHO, —$OC_{1-6}$ alkyl, —$S(O)_mC_{1-6}$ alkyl, —$NH_2$, —$NHC_{1-6}$ alkyl, —$N(C_{1-6}$ alkyl$)_2$, —$C(O)C_{1-6}$ alkyl, —$CO_2H$, —$CO_2C_{1-6}$ alkyl, —$C(O)NH_2$, —$C(O)NHC_{1-6}$ alkyl, —$C(O)N(C_{1-6}$ alkyl$)_2$, —$OC(O)C_{1-6}$ alkyl, —$NHC(O)C_{1-6}$ alkyl, —$S(O)_mNH_2$, —$S(O)_mNHC_{1-6}$ alkyl, —$S(O)_m(C_{1-6}$ alkyl$)_2$, aryl, heteroaryl and heterocyclyl.

Pharmaceutical compositions and methods of treatment are also included.

DETAILED DESCRIPTION OF THE INVENTION

The present invention relates to compounds of formula I, as well as tautomers, salts, hydrates and prodrugs thereof.

The invention is described herein in detail using terms that are defined below unless otherwise specified.

The term "alkyl" and the alkyl portions of aralkyl, alkoxy and the like refer to a monovalent alkane (hydrocarbon) derived radical containing from 1 to 15 carbon atoms unless otherwise defined. It may be straight, branched or cyclic. Preferred straight or branched alkyl groups include methyl, ethyl, propyl, isopropyl, butyl and t-butyl. Preferred cycloalkyl groups include cyclopentyl and cyclohexyl.

Alkyl also includes a straight or branched alkyl group which contains or is interrupted by a cycloalkylene portion. Examples include the following:

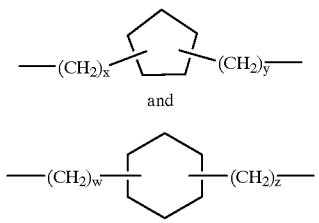

wherein: x and y=from 0–10; and w and z=from 0–9.

The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups as defined with respect to each variable.

The term "alkenyl" refers to a hydrocarbon radical straight, branched or cyclic containing from 2 to 15 carbon atoms and at least one carbon to carbon double bond. Preferably one carbon to carbon double bond is present, and up to four non-aromatic (non-resonating) carbon-carbon double bonds may be present. Preferred alkenyl groups include ethenyl, propenyl, butenyl and cyclohexenyl. As described above with respect to alkyl, the straight, branched or cyclic portion of the alkenyl group may contain double bonds and may be substituted when a substituted alkenyl group is provided.

The term "alkynyl" refers to a hydrocarbon radical straight, branched or cyclic, containing from 2 to 15 carbon atoms and at least one carbon to carbon triple bond. Up to three carbon-carbon triple bonds may be present. Preferred alkynyl groups include ethynyl, propynyl and butynyl. As described above with respect to alkyl, the straight, branched or cyclic portion of the alkynyl group may contain triple bonds and may be substituted when a substituted alkynyl group is provided.

The term "alkoxy" refers to those groups of the designated carbon length in either a straight or branched configuration attached through an oxygen linkage and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy, allyloxy, propargyloxy, and the like.

The term halo as used herein means fluoro, chloro, bromo or iodo.

Aryl refers to aromatic rings e.g., phenyl, substituted phenyl and like groups as well as rings which are fused, e.g., naphthyl and the like. Aryl thus contains at least one ring having at least 5 atoms, with up to two such rings being present, containing up to 10 atoms therein, with alternating (resonating) double bonds between adjacent carbon atoms. The preferred aryl groups are phenyl and naphthyl. Aryl groups may likewise be substituted. Preferred substituted aryls include phenyl and naphthyl substituted with up to three $R^a$ groups.

Heteroaryl is a group containing from 5 to 10 atoms, 1–4 of which are heteroatoms, 0–4 of which heteroatoms are N and 0–1 of which are O or $S(O)_m$, said heteroaryl group being unsubstituted or substituted with up to 3 $R^a$ groups; examples are pyrrolyl, furanyl, thienyl, pyridyl, quinolinyl, purinyl, imidazolyl, imidazopyridyl and pyrimidinyl.

Tautomers as used herein, refer to the following structures:

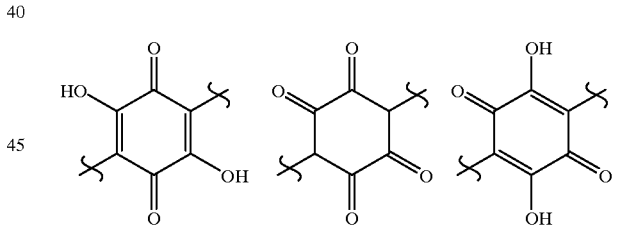

Additionally, in the compound of formula I when X equals N, the following structure is an example of a tautomer that is included:

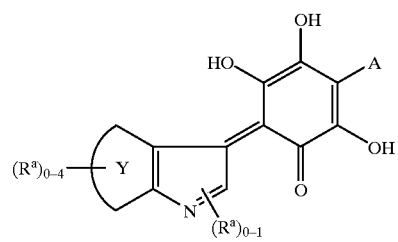

These and others are included in the present invention.

Reduced forms of the compounds refer to the following structure:

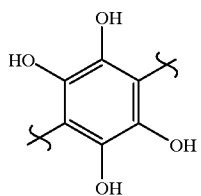

These are also included in the present invention.

Prodrugs as used herein refer to $C_{1-4}$ alkoxy, $C_{1-4}$ acyloxy, carboxylic acid and phosphate derivatives of the compounds of formula I as well as other compounds which generate quinones in vivo. Examples of prodrugs include the following:

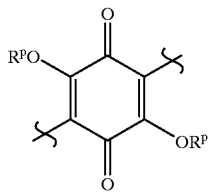

wherein at least one Rp represents $C_{1-4}$ alkyl, $C_{1-4}$ acyl, $CO_2H$, a phosphate group, a metal complex, such as a chelating metal, or another group which generates the quinone in vivo.

A subset of compounds that is of particular interest is described with reference to formula I wherein:

represents a phenyl ring. Within this subset of compounds, all other variables are as originally defined.

Another subset of compounds that is of particular interest is described with reference to formula I wherein:

represents a pyrrole ring. Within this subset of compounds, all other variables are as originally defined.

Another subset of compounds that is of particular interest is described with reference to formula I wherein:

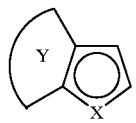 represents 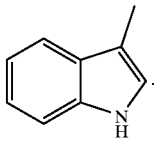

Within this subset, all other variables are as originally defined.

Another subset of compounds that is of particular interest is described with reference to formula I wherein:

1–4 $R^a$ groups are present, and each $R^a$ is independently selected from the group consisting of:

halo, —OH, —$C_{1-12}$ alkyl($R^b$)$_3$, —$C_{2-10}$ alkenyl($R^b$)$_3$, —$C_{2-10}$ alkynyl($R^b$)$_3$, —$C_{6-10}$ aryl($R^b$)$_3$, -heteroaryl($R^b$)$_3$, -heterocyclyl($R^b$)$_3$, —$NH_2$, —$NHC_{1-6}$ alkyl($R^b$)$_3$, —N($C_{1-6}$ alkyl($R^b$)$_3$)$_2$, —$N_3$, —$OC_{1-6}$ alkyl($R^b$)$_3$, —S(O)$_m$H, —S(O)$_m$$C_{1-6}$ alkyl($R^b$)$_3$, —CHO, —C(O)$C_{1-6}$ alkyl($R^b$)$_3$, —$CO_2H$, —C(O)O$C_{1-6}$ alkyl($R^b$)$_3$, —C(O)S$C_{1-6}$ alkyl($R^b$)$_3$, —C(O)$NH_2$, —C(O)NH$C_{1-6}$ alkyl($R^b$)$_3$, —NHC(O)$C_{1-6}$ alkyl($R^b$)$_3$, —S(O)$_m$$NH_2$, —NHS(O)$_m$$C_{1-6}$ alkyl($R^b$)$_3$, —S(O)$_m$NH$C_{1-6}$ alkyl($R^b$)$_3$ and —S(O)$_m$N($C_{1-6}$ alkyl($R^b$)$_3$)$_2$, and each $R^b$ is independently selected from: H, OH, halo, —$C_{1-4}$ alkyl, —$C_{2-4}$ alkenyl, —$C_{2-4}$ alkynyl, —$CF_3$, —$OCF_3$, —$NO_2$, —$N_3$, —CHO, —$OC_{1-6}$ alkyl, —S(O)$_m$$C_{1-6}$ alkyl, —$NH_2$, —NH$C_{1-6}$ alkyl, —N($C_{1-6}$ alkyl)$_2$, —C(O)$C_{1-6}$ alkyl, —$CO_2H$, —$CO_2$$C_{1-6}$ alkyl, —C(O)$NH_2$, —C(O)NH$C_{1-6}$ alkyl, —C(O)N($C_{1-6}$ alkyl)$_2$, —OC(O)$C_{1-6}$ alkyl, —NHC(O)$C_{1-6}$ alkyl, —S(O)$_m$$NH_2$, —S(O)$_m$NH$C_{1-6}$ alkyl, —S(O)$_m$($C_{1-6}$ alkyl)$_2$, aryl, heteroaryl and heterocyclyl. Within this subset of compounds, all other variables are as originally defined.

Another subset of compounds that is of particular interest is described with reference to formula I wherein:

A represents a member selected from the group consisting of:
 a 5–10 membered mono- or bicyclic aryl group or
 a 9–10 membered bicyclic heteroaryl group, attachment to which is through a 6 membered ring, the heteroaryl groups having 1–4 heteroatoms selected from O, S(O)$_m$ and N,
 said aryl and heteroaryl groups being optionally substituted with 1–3 $R^a$ groups. Within this subset of compounds, all other variables are as originally defined.

More particularly, a subset of compounds that is of particular interest is described with reference to formula I wherein A represents an aryl group selected from phenyl and naphthyl, optionally substituted with 1–3 $R^a$ groups. Within this subset, all other variables are as originally defined.

More particularly, another subset of compounds that is of particular interest is described with reference to formula I wherein A represents a 9–10 membered bicyclic heteroaryl group, attachment to which is through a 6 membered ring, the heteroaryl group having 1–4 heteroatoms selected from O, S(O)$_m$ and N,
 said heteroaryl group being optionally substituted with 1–3 $R^a$ groups. Within this subset of compounds, all other variables are as originally defined. Examples of preferred values of A which are 9–10 membered bicyclic heteroaryl groups include the following:

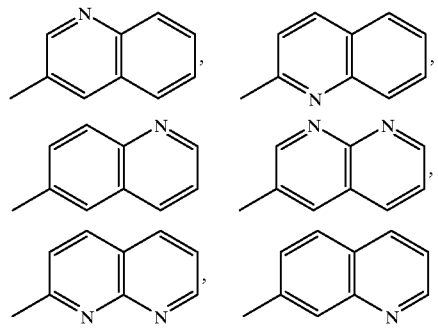

-continued

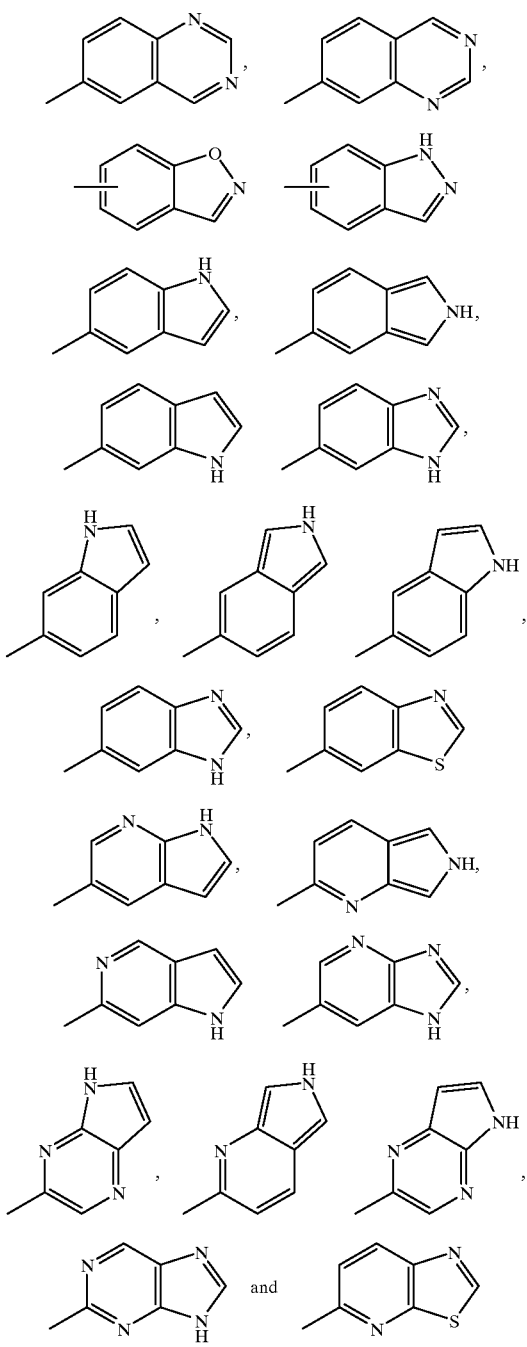

More particularly, another subset of compounds that is of particular interest is described with reference to formula I wherein A represents a 5–6 membered isolated monocyclic heteroaryl group, having 1–3 heteroatoms selected from O, $S(O)_m$ and N, optionally substituted with 1–3 $R^a$ groups. Examples of preferred 5–6 membered isolated monocyclic heteroaryl groups include pyrrole, imidazole, triazole, pyridine, pyrimidine, pyrazine, furan, thiophene, oxazole and thiazole.

Another subset of compounds that is of particular interest is described with reference to formula I wherein the moiety:

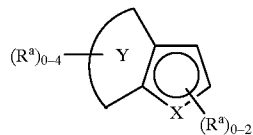

has 1–4 $R^a$ groups attached, said $R^a$ groups being selected from the group consisting of:

halo, $—C_{1-12}$ alkyl$(R^b)_3$, $—NH_2$, $—NHC_{1-6}$ alkyl$(R^b)_3$, $—N(C_{1-6}$ alkyl$(R^b)_3)_2$, $—N_3$, $—OC_{1-6}$ alkyl$(R^b)_3$, $—S(O)_mH$, $—S(O)_mC_{1-6}$ alkyl$(R^b)_3$, $—C(O)C_{1-6}$ alkyl$(R^b)_3$, $—CO_2H$, $—C(O)OC_{1-6}$ alkyl$(R^b)_3$, $—C(O)NH_2$, $—C(O)NHC_{1-6}$ alkyl$(R^b)_3$, $—NHC(O)C_{1-6}$ alkyl$(R^b)_3$, $—S(O)_mNH_2$, $—NHS(O)_mC_{1-6}$ alkyl$(R^b)_3$, $—S(O)_mNHC_{1-6}$ alkyl$(R^b)_3$ and $—S(O)_mN(C_{1-6}$ alkyl$(R^b)_3)_2$, and each $R^b$ is independently selected from: H, OH, halo, $—CF_3$, $—OCF_3$, $—NO_2$, $—N_3$, $—OC_{1-6}$ alkyl, $—S(O)_mC_{1-6}$ alkyl, $—NH_2$, $—NHC_{1-6}$ alkyl, $—N(C_{1-6}$ alkyl$)_2$, $—C(O)C_{1-6}$ alkyl, $—CO_2H$, $—CO_2C_{1-6}$ alkyl, $—C(O)NH_2$, $—C(O)NHC_{1-6}$ alkyl, $—C(O)N(C_{1-6}$ alkyl$)_2$, $—NHC(O)C_{1-6}$ alkyl, $—S(O)_mNH_2$, $—S(O)_mNHC_{1-6}$ alkyl, $—S(O)_m(C_{1-6}$ alkyl$)_2$, aryl, heteroaryl and heterocyclyl. Within this subset of compounds, all other variables are as originally defined.

Another subset of compounds that is of particular interest relates to compounds of formula I wherein A represents a phenyl ring, unsubstituted or substituted with 1–3 $R^a$ moieties selected from the group consisting of:

halo, $—C_{1-12}$ alkyl$(R^b)_3$, $—NH_2$, $—NHC_{1-6}$ alkyl$(R^b)_3$, $—N(C_{1-6}$ alkyl$(R^b)_3)_2$, $—N_3$, $—OC_{1-6}$ alkyl$(R^b)_3$, $—S(O)_mH$, $—S(O)_mC_{1-6}$ alkyl$(R^b)_3$, $—C(O)C_{1-6}$ alkyl$(R^b)_3$, $—CO_2H$, $—C(O)OC_{1-6}$ alkyl$(R^b)_3$, $—C(O)NH_2$, $—C(O)NHC_{1-6}$ alkyl$(R^b)_3$, $—NHC(O)C_{1-6}$ alkyl$(R^b)_3$, $—S(O)_mNH_2$, $—NHS(O)_mC_{1-6}$ alkyl$(R^b)_3$, $—S(O)_mNHC_{1-6}$ alkyl$(R^b)_3$ and $—S(O)_mN(C_{1-6}$ alkyl$(R^b)_3)_2$, and each $R^b$ is independently selected from: H, OH, halo, $—CF_3$, $—OCF_3$, $—NO_2$, $—N_3$, $—OC_{1-6}$ alkyl, $—S(O)_mC_{1-6}$ alkyl, $—NH_2$, $—NHC_{1-6}$ alkyl, $—N(C_{1-6}$ alkyl$)_2$, $—C(O)C_{1-6}$ alkyl, $—CO_2H$, $—CO_2C_{1-6}$ alkyl, $—C(O)NH_2$, $—C(O)NHC_{1-6}$ alkyl, $—C(O)N(C_{1-6}$ alkyl$)_2$, $—NHC(O)C_{1-6}$ alkyl, $—S(O)_mNH_2$, $—S(O)_mNHC_{1-6}$ alkyl, $—S(O)_m(C_{1-6}$ alkyl$)_2$, aryl, heteroaryl and heterocyclyl. Within this subset of compounds, all other variables are as originally defined.

More particularly, a subset of compounds that is of particular interest relates to compounds of formula Ia:

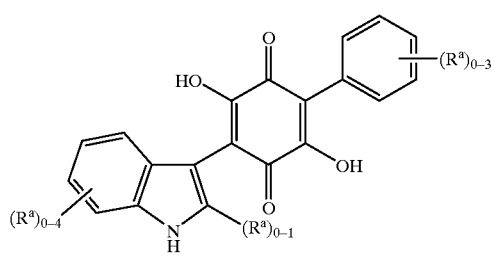

Ia with $R^a$ as originally defined.

Another subset of compounds that is of particular interest relates to compounds of formula Ib:

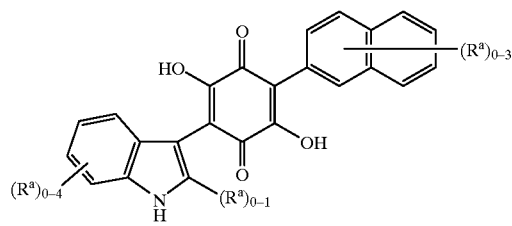

Ib with $R^a$ as originally defined.

More preferably, the compounds of formula Ia and Ib above are described wherein:

0–3 Ra groups are present in the molecule and are selected from the group consisting of: halo, —$C_{1-12}$ alkyl($R^b$)$_3$, —$NH_2$, —$NHC_{1-6}$ alkyl($R^b$)$_3$, —$N(C_{1-6}$ alkyl($R^b$)$_3$)$_2$, —$N_3$, —$OC_{1-6}$ alkyl($R^b$)$_3$, —$S(O)_mH$, —$S(O)_mC_{1-6}$ alkyl($R^b$)$_3$, —$C(O)C_{1-6}$ alkyl($R^b$)$_3$, —$CO_2H$, —$C(O)OC_{1-6}$ alkyl($R^b$)$_3$, —$C(O)NH_2$, —$C(O)NHC_{1-6}$ alkyl($R^b$)$_3$, —$NHC(O)C_{1-6}$ alkyl($R^b$)$_3$, —$S(O)_mNH_2$, —$NHS(O)_mC_{1-6}$ alkyl($R^b$)$_3$, —$S(O)_mNHC_{1-6}$ alkyl($R^b$)$_3$ and —$S(O)_mN(C_{1-6}$ alkyl($R^b$)$_3$)$_2$, and each $R^b$ is independently selected from: H, OH, halo, —$CF_3$, —$OCF_3$, —$NO_2$, —$N_3$, —$OC_{1-6}$ alkyl, —$S(O)_mC_{1-6}$ alkyl, —$NH_2$, —$NHC_{1-6}$ alkyl, —$N(C_{1-6}$ alkyl)$_2$, —$C(O)C_{1-6}$ alkyl, —$CO_2H$, —$CO_2C_{1-6}$ alkyl, —$C(O)NH_2$, —$C(O)NHC_{1-6}$ alkyl, —$C(O)N(C_{1-6}$ alkyl)$_2$, —$NHC(O)C_{1-6}$ alkyl, —$S(O)_mNH_2$, —$S(O)_mNHC_{1-6}$ alkyl, —$S(O)_m(C_{1-6}$ alkyl)$_2$, aryl, heteroaryl and heterocyclyl, and m is 0, 1 or 2.

Representative examples of the compounds of formula I are shown below in Table I.

TABLE I

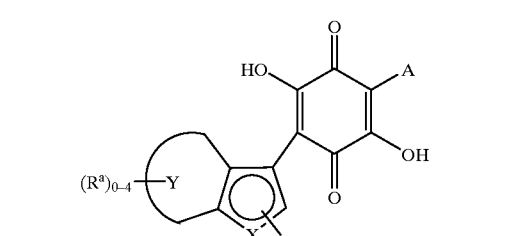

I

| | A |
|---|---|
| 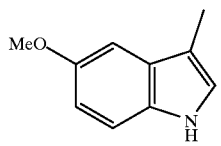 | 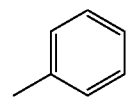 |

TABLE I-continued

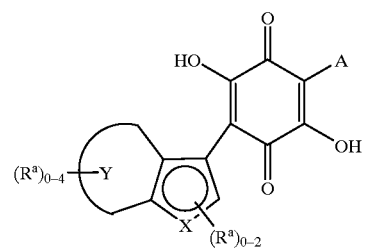

I

| | A |
|---|---|
| 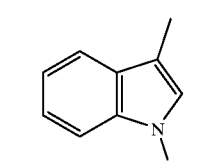 | 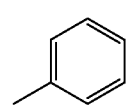 |
| 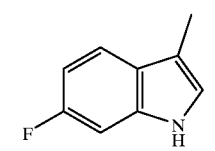 | 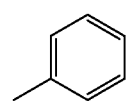 |

TABLE I-continued

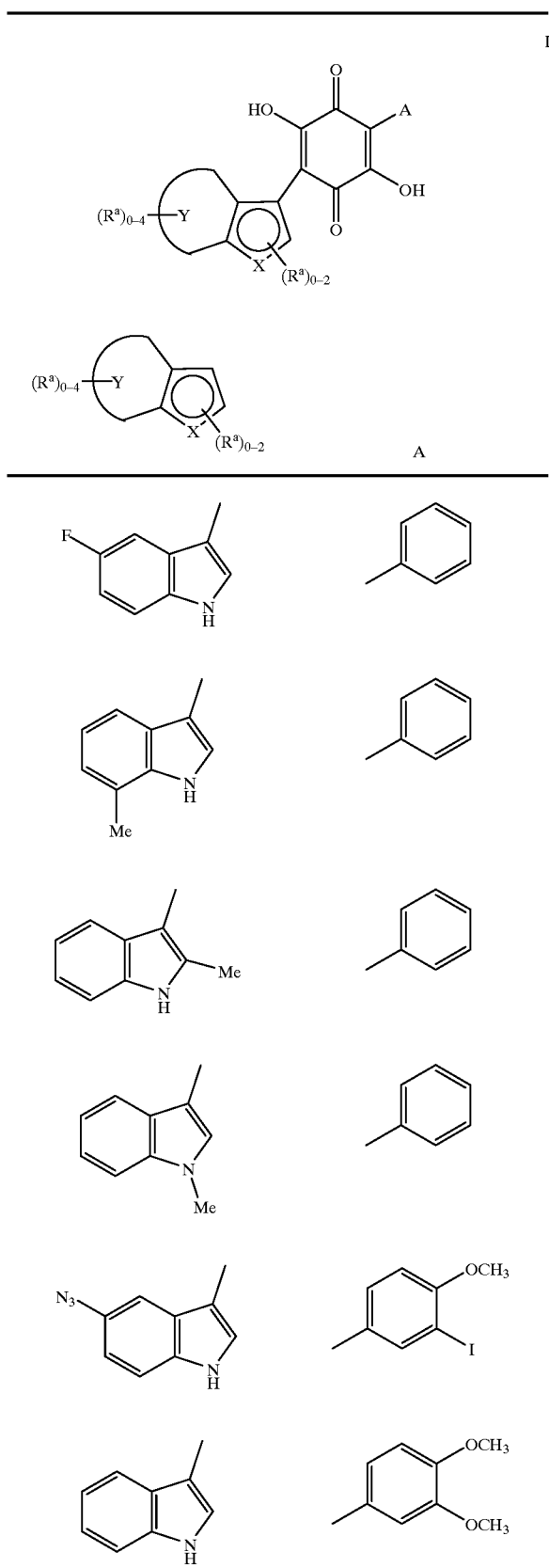

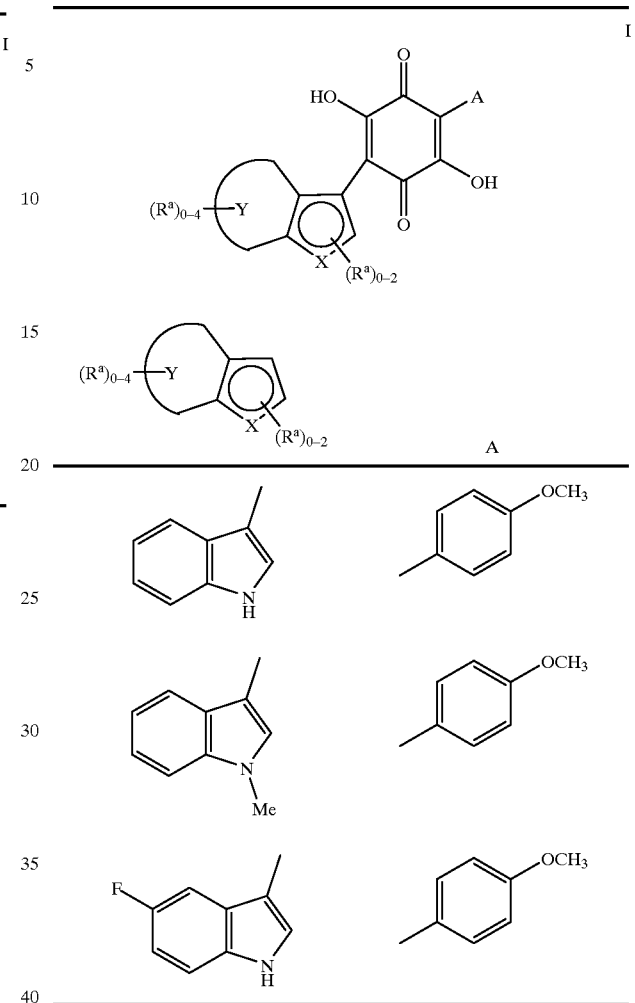

Throughout the instant application, the following abbreviations are used with the following meanings:

| | |
|---|---|
| Bu | butyl |
| Bn | benzyl |
| BOC, Boc | t-butyloxycarbonyl |
| BOP | Benzotriazol-1-yloxy tris(dimethylamino)-phosphonium hexafluorophosphate |
| calc. | calculated |
| CBZ, Cbz | Benzyloxycarbonyl |
| CDI | N,N'-carbonyl diimidazole |
| DCC | Dicyclohexylcarbodiimide |
| DCM | dichloromethane |
| DIEA | diisopropylethylamine |
| DMF | N,N-dimethylformamide |
| DMAP | 4-Dimethylaminopyridine |
| DSC | N,N'-disuccinimidyl carbonate |
| EDC | 1-(3-dimethylaminopropyl)-3-ethylcarbodi-imide hydrochloride |
| EI-MS | Electron ion-mass spectroscopy |
| Et | ethyl |
| EtOAc | ethyl acetate |
| EtOH | ethanol |
| eq. | equivalent(s) |
| FAB-MS | Fast atom bombardment-mass spectroscopy |
| HOAc | acetic acid |
| HOBT, HOBt | Hydroxybenztriazole |
| HPLC | High pressure liquid chromatography |

-continued

| | |
|---|---|
| KHMDS | Potassium bis(trimethylsilyl)amide |
| LAH | Lithium aluminum hydride |
| LHMDS | Lithium bis(trimethylsilyl)amide |
| Me | methyl |
| MeOH | methanol |
| MF | Molecular formula |
| MHz | Megahertz |
| MPLC | Medium pressure liquid chromatography |
| NMM | N-Methylmorpholine |
| NMR | Nuclear Magnetic Resonance |
| Ph | phenyl |
| Pr | propyl |
| prep. | prepared |
| TFA | Trifluoroacetic acid |
| THF | Tetrahydrofuran |
| TLC | Thin layer chromatography |
| TMS | Trimethylsilane |

Specific compounds may require the use of protecting groups to enable their successful elaboration into the desired structure. Protecting groups may be chosen with, e.g., reference to Greene, T. W., et al., *Protective Groups in Organic Synthesis*, John Wiley & Sons, Inc., 1991. The blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with fluoride ion, treatment with a transition metal catalyst and a nucleophile, and catalytic hydrogenation.

Non-limiting examples of suitable hydroxyl protecting groups are: trimethylsilyl, triethylsilyl, o-nitrobenzyloxycarbonyl, p-nitrobenzyloxycarbonyl, t-butyldiphenylsilyl, t-butyldimethylsilyl, benzyloxycarbonyl, t-butyloxycarbonyl, 2,2,2-trichloroethyloxycarbonyl, and allyloxycarbonyl. Non-limiting examples of suitable carboxyl protecting groups are benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl and t-butyl.

Salts encompassed within the term "pharmaceutically acceptable salts" refer to non-toxic salts of the compounds of this invention which are generally prepared by reacting the free base with a suitable organic or inorganic acid. Representative salts and esters include the following:

Acetate, Benzenesulfonate, Benzoate, Bicarbonate, Bisulfate, Bitartrate, Borate, Camsylate, Carbonate, Citrate, Dihydrochloride, Edetate, Edisylate, Estolate, Esylate, Fumarate, Gluconate, Glutamate, Hydrobromide, Hydrochloride, Hydroxynaphthoate, Lactate, Lactobionate, Laurate, Malate, Maleate, Mandelate, Mesylate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Tosylate, and Valerate.

The compounds of the present invention may contain one or more asymmetric carbon atoms and may exist in racemic and optically active forms. All of these compounds are contemplated to be within the scope of the present invention. Therefore, where a compound is chiral, the separate enantiomers, substantially free of the other, are included within the scope of the invention; further included are all mixtures of the two enantiomers. Also included within the scope of the invention are polymorphs and hydrates of the compounds of the instant invention.

Asymmetric centers may be present in the compounds of the instant invention depending upon the nature of the various substituents on the molecule. Each such asymmetric center will independently produce two optical isomers and it is intended that all of the possible optical isomers and diastereomers in mixture and as pure or partially purified compounds are included within the ambit of this invention. Tautomeric forms of the compounds of formula I are also included herein. Tautomeric forms as used herein refer to structures which differ by the shift of double bonds and concomitant displacement of hydrogen atoms.

The present invention also provides a method for treating or preventing the onset of diabetes mellitis in a mammalian patient which comprises administering to said mammal a compound of formula I in an amount which is effective for modulating insulin receptor tyrosine kinase activity.

The present invention further provides a method for reducing blood glucose levels in a mammalian patient in need thereof, which comprises administering to said mammal a glucose reducing effective amount of a compound of formula I or a pharmaceutically acceptable salt, hydrate or tautomer thereof, in an amount which is effective for modulating insulin receptor tyrosine kinase activity.

Yet another aspect of the present invention provides pharmaceutical compositions containing a compound of formula I and a pharmaceutically acceptable carrier.

The term "to modulate insulin receptor tyrosine kinase activity" includes activating insulin receptor tyrosine kinase, stimulating insulin receptor tyrosine phosphorylation, or enhancing the effect of insulin to stimulate insulin receptor tyrosine kinase activity or insulin signal transduction pathway. The ability of the compound to modulate insulin receptor tyrosine activity may be determined using the methods described herein. Briefly, Chinese Hamster Ovary (CHO) cells expressing human insulin receptor are plated and treated with insulin and/or test agents. CHO.T cells are one type of CHO cells that express human insulin receptor. The treated cells are lysed, and the insulin receptor is purified. The level of tyrosine phosphorylation of the receptor is determined using an anti-phosphotyrosine antibody conjugated to alkaline phosphatase and its chromogenic substrate. The insulin receptor tyrosine kinase activity (IRTK) is determined using an exogenous substrate and $\gamma$-$^{32}$P-ATP. Although the procedures described in the Examples utilize CHO.T cells, cell lines similar to the CHO.T cells described herein may be prepared by one skilled in the art. For example, NIH3T3 cells, COS cells, Rat-1 cells and other appropriate fibroblasts transfected with cDNA encoding human insulin receptor can also be used in the assays.

The concept of altered levels of insulin, biological activity of insulin, and levels of insulin sensitivity includes impaired insulin production and/or activity, lower than normal levels of endogenous insulin, resistance to normal or elevated level of insulin, which may be due to insufficient insulin receptor expression, reduced insulin-binding affinity, or any abnormality at any step along the insulin signaling pathway.

The compounds of formula I modulate insulin receptor tyrosine kinase activity and are thus useful in the treatment, prevention, amelioration, suppression or control of diseases, disorders or conditions that are characterized by altered insulin levels, biological activity of insulin, insulin sensitivity, or a combination thereof. Such diseases or disorders include diabetes mellitus (Type I and Type II), atherosclerosis, hypertension, lipid disorders, obesity, polycystic ovarian syndrome, and other conditions associated with insulin deficiency or insulin resistance. These compounds are also useful in the treatment or prevention of hyperglycemia or for controlling blood glucose levels in an animal suffering from Type I or Type II diabetes mellitus.

Without being bound by a particular theory, it is believed that the compounds stimulate insulin receptor tyrosine kinase activity. In addition, these compounds stimulate tyrosine phosphorylation of insulin receptor β subunit and insulin receptor substrate-1 as well as activity of phosphoinositide-3-kinase. These compounds have the properties of an insulin mimetic and insulin sensitizing agent.

Dose Ranges

The effective dosage of active ingredient employed may vary depending on the particular compound employed, the mode of administration, the condition being treated and the severity of the condition being treated. Although the compounds may be administered by any conventional mode of administration, including intravenous, intramuscular, subcutaneous, oral, topical, etc.; oral administration is preferred.

When treating or preventing diabetes mellitus and/or hyperglycemia generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

Pharmaceutical Composition

Another aspect of the present invention provides pharmaceutical compositions which comprise a compound of formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, additional active ingredient(s) and pharmaceutically acceptable excipients.

The pharmaceutical compositions of the present invention comprise a compound of formula I as an active ingredient, and may also contain a pharmaceutically acceptable carrier and optionally other therapeutic ingredients. The compositions include compositions suitable for oral, rectal, topical, and parenteral (including subcutaneous, intramuscular, and intravenous) administrations, although the most suitable route in any given case will depend on the particular host, and nature and severity of the conditions for which the active ingredient is being administered. The pharmaceutical compositions may be conveniently presented in unit dosage form and prepared by any of the methods well-known in the art of pharmacy.

In practical use, a compound of the invention can be combined with a pharmaceutical carrier according to conventional pharmaceutical compounding techniques. The carrier may take a wide variety of forms depending on the form of preparation desired for administration, e.g., oral or parenteral (including intravenous).

In preparing the compositions for oral dosage form, any of the usual pharmaceutical media may be employed. For example, in the case of oral liquid preparations such as suspensions, elixirs and solutions, water, glycols, oils, alcohols, flavoring agents, preservatives, coloring agents and the like may be used; or in the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which case solid pharmaceutical carriers are obviously employed. If desired, tablets may be coated by standard aqueous or nonaqueous techniques. In addition to the common dosage forms set out above, the active ingredient may also be administered by controlled release means and/or delivery devices.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any conventional method. In general, the compositions are prepared by admixing the active ingredient with a liquid or finely divided solid or both, and then, if necessary, shaping the product into the desired preparation. For example, a tablet may be prepared by compression or molding, optionally with one or more accessory ingredients. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Pharmaceutical compositions of the present invention suitable for parenteral administration may be prepared as solutions or suspensions of these active compounds in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Suitable topical formulations include transdermal devices, aerosols, creams, ointments, lotions, dusting powders, and the like. These formulations may be prepared via conventional methods containing the active ingredient. To illustrate, a cream or ointment is prepared by mixing sufficient quantities of hydrophilic material and water, containing from about 0.5–90% by weight of the compound, in sufficient quantities to produce a cream or ointment having the desired consistency.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the combination with the softened or melted carrier(s) followed by chilling and shaping moulds.

It should be understood that in addition to the aforementioned carrier ingredients the pharmaceutical formulations described above may include, as appropriate, one or more additional carrier ingredients such as diluents, buffers, flavoring agents, binders, surface-active agents, thickeners, lubricants, preservatives (including anti-oxidants) and the like, and substances included for the purpose of rendering the formulation isotonic with the blood of the intended recipient.

Combination Therapy

The compounds of the present invention may be used in combination with other drugs. Such other drugs may be administered, by a route and in an amount commonly used, contemporaneously or sequentially. When a compound of formula I is used contemporaneously with one or more other drugs, a pharmaceutical composition containing such other drugs in addition to the compound of the invention is preferred. Accordingly, the pharmaceutical compositions of the present invention include those that also contain one or more other active ingredients, in addition to a compound of formula I. Examples of other active ingredients that are administered separately or in the same pharmaceutical compositions, include, but are not limited to antidiabetic agents such as insulin, sulfonylureas, biguanides (such as metformin) α-glucosidase inhibitors (such as acarbose), and peroxisome proliferator-activater receptor γ agonists such as the glitazones (thiazolidinediones such as pioglitazone, troglitazone, MCC-555, and BRL49653); cholesterol lowering agents such as HMG-CoA reductase inhibitors (lovastatin, simvastatin, pravastatin, fluvastatin, atorvastatin and others), sequestrants (cholestyramine, colestipol and dialkylaminoalkyl derivatives of a cross-linked dextran), nicotinyl alcohol nicotinic acid or a salt thereof, proliferator-activater receptor a agonists such as fenofibric acid derivatives (gemfibrozil, clofibrate, fenofibrate and benzafibrate), and probucol.

The compounds of Formula I of the present invention can be prepared according to the following schemes, or using routine modifications thereof. The definitions of the variables are as originally described unless otherwise stated.

Scheme 1

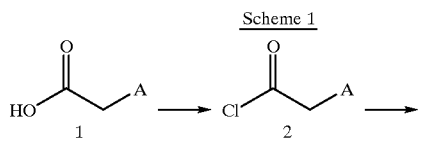

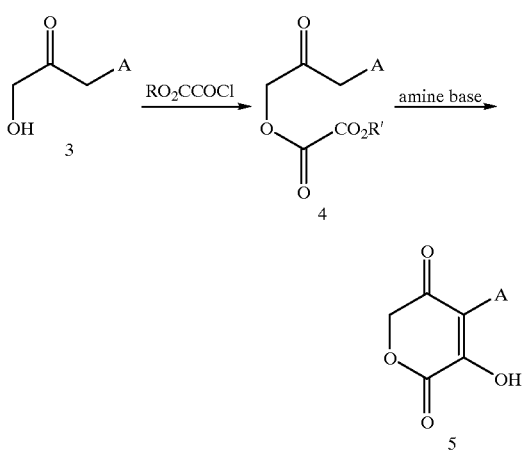

Intermediates of Formula 5 can be synthesized according to Scheme 1. Acid chlorides 2 are commercially available or can be prepared from the corresponding acids 1 using oxalyl chloride or thionyl chloride under standard reaction conditions. Transformation of acid chlorides 2 to α-hydroxy ketones 3 can be carried out using the method described in *J. Org. Chem.*, 44, 4617–4622 (1979).

Introduction of the oxalate group can be achieved using alkyl oxalyl chloride, such as ethyl oxalyl chloride. Ring closure can be effected by DBU or its equivalent to afford intermediate 5, which can be used for the synthesis of the compounds of Formula I as shown in Scheme 3.

Scheme 2

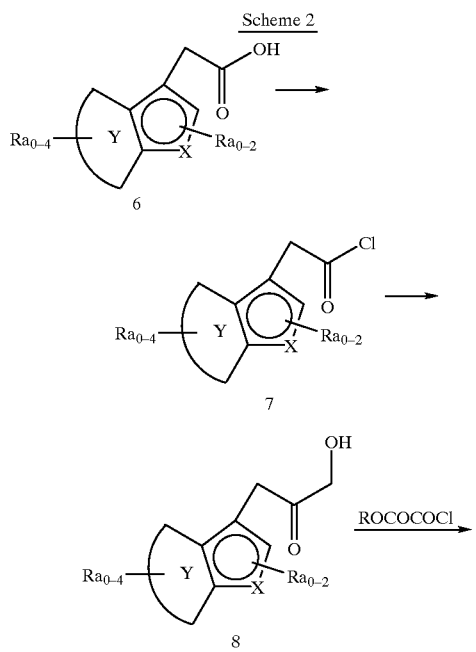

-continued

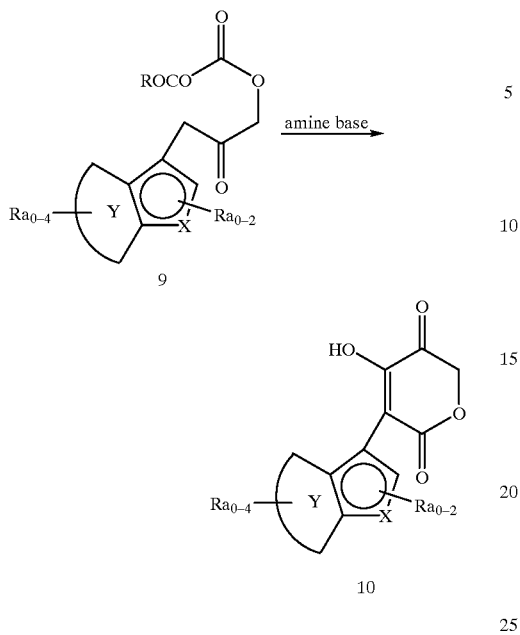

As shown in the Scheme 2, the intermediates of Formula 10 can be prepared similarly to intermediates of Formula 5, starting from acids 6.

Scheme 3

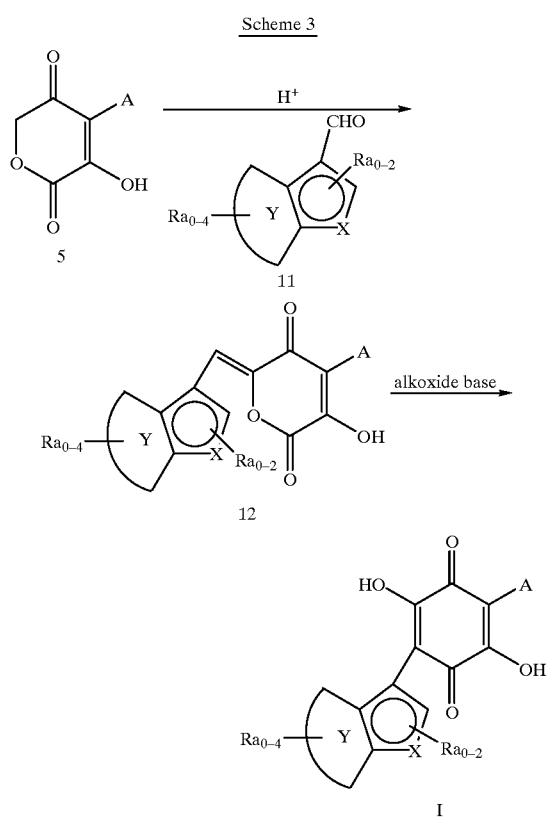

Intermediates of Formula 5 can be coupled to intermediates of Formula 11 to afford compounds of Formula 12 under acidic conditions (see *Liebigs Ann. Chem.* 177–194 (1986)). The aldehydes of Formula 11 are commercially available, known in the literature or can be prepared following literature methods. Rearrangement of compounds 12 to the products of Formula I can be effected using an alkoxide base such as sodium methoxide and sodium ethoxide.

Scheme 4

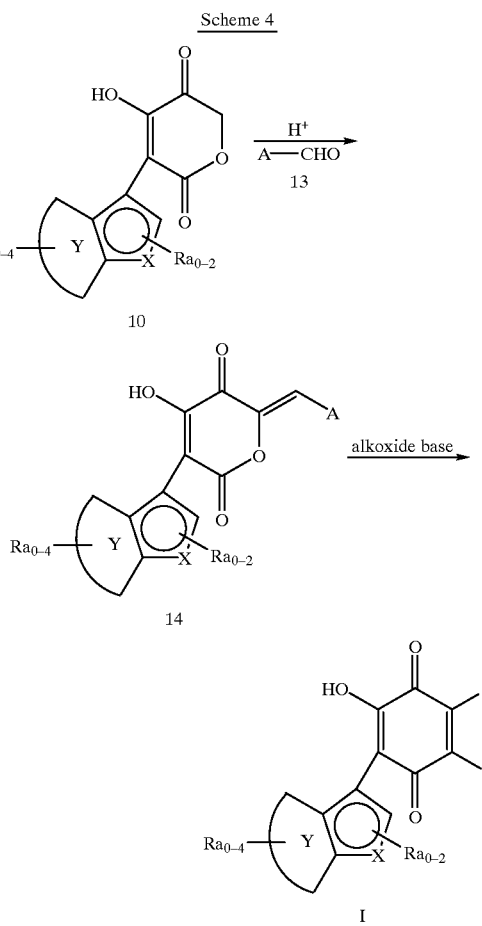

Alternatively, compounds of Formula I can be prepared starting from intermediates of Formula 10 and aldehydes of Formula 13. Aldehyde 13 is commercially available, known in the literature or can be prepared following literature methods described for analogous compounds. Condensation of compounds 10 and 13 leads to products of Formula 14, which can be rearranged using alkoxide bases.

Compounds of formula I can be prepared using the synthetic route depicted in Scheme 3 or 4.

The invention can be further illustrated in connection with the following non-limiting examples. All temperature are degrees Celsius unless noted otherwise.

PREPARATIVE EXAMPLE 1

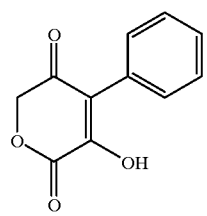

Step A

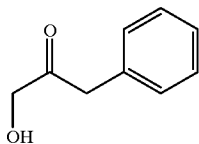

To a mixture of phenylacetyl chloride (3.1 g, 20 mmol) and tris(trimethylsilyloxy)ethylene (13.5 g, 44 mmol) at room temperature was added three drops of neat $SnCl_4$ via syringe. The reaction mixture was stirred for 3 h before it was poured into a mixture of dioxane (25 mL) and 0.6 N HCl aqueous solution (10 mL). The mixture was stirred at 90° C. for 10 min, cooled to room temperature, and extracted twice with $Et_2O$. The combined organic layers were washed with saturated solution of $NaHCO_3$ and brine, dried over anhydrous $MgSO_4$, filtered, and concentrated in vacuo. The residue was crystallized from hexanes to give 2.47 g of the desired product as a white solid.

$^1$H NMR ($CDCl_3$, 400 MHz) δ7.35–7.15 (m, 5H, $C_6H_5$), 4.26 (d, 2H, $CH_2O$), 3.70 (s, 2H, $CH_2CO$), 3.00 (t, 1H, OH).

Step B

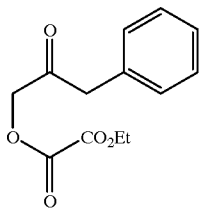

To a solution of the intermediate from the previous step (2.47 g, 16.4 mmol) in THF (120 mL) at 0° C. was added $Et_3N$ (2.7 mL, 19 mmol), followed by ethyl oxalyl chloride (1.9 mL, 17 mmol). The mixture was stirred at 0° C. for 3 h, poured into EtOAc (200 mL), washed with water and brine, dried over anhydrous $MgSO_4$, filtered, and concentrated in vacuo to give 3.9 g of the crude product as a slightly yellow oil, which was used in the next step without further purification.

$^1$H NMR ($CDCl_3$, 400 MHz) δ7.35–7.15 (m, 5H, $C_6H_5$), 4.85 (s, 2H, $CH_2O$), 4.37 (q, 2H, $COOCH_2$), 3.77 (s, 2H, $PhCH_2CO$), 1.38 (t, 3H, $CH_3$).

Step C

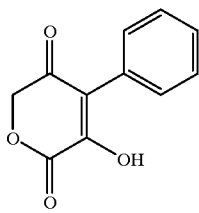

To a solution of DBU (4.9 mL, 32.8 mL) in DMF (16 mL) at −20° C. was added dropwise a solution of the crude intermediate from the previous step (3.9 g, 16 mmol) in DMF (16 mL). The reaction mixture was stirred at −15° C. for 2.5 h before it was poured slowly into an ice-cold 1.0 N HCl solution (100 mL). The crystalline product (1.85 g) was collected by filtration, washed thoroughly with water, and dried under high vacuum. The mother liquid was extracted with EtOAc. The extract was washed with water and brine, dried over $MgSO_4$, filtered and concentrated. The residue was purified by recrystallization from $CH_2Cl_2$/hexanes to give another 0.57 g of the product as slightly yellow solid. The total yield was 2.42 g (two steps).

$^1$H NMR (Acetone-$d_6$, 400 MHz) δ7.50–7.30 (m, 5H, $C_6H_5$), 5.11 (s, 2H, $OCH_2$).

PREPARATIVE EXAMPLE 2

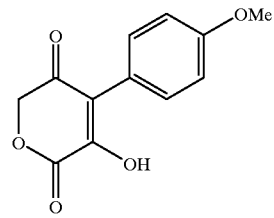

Using the procedure set forth in Preparative Example I, and substituting 4-methoxyphenylacetyl chloride for phenylacetyl chloride, the target compound was prepared.

$^1$H NMR (Acetone-$d_6$, 400 MHz) δ7.47 (d, J=9.0 Hz, 2H), 6.95 (d, J=9.0 Hz, 2H), 5.08 (s, 2H, $OCH_2CO$), 3.82 (s, 3H, $OCH_3$). CI-MS calc. for $C_{12}HO_5$ (M+H): 235; Found: 235.

PREPARATIVE EXAMPLE 3

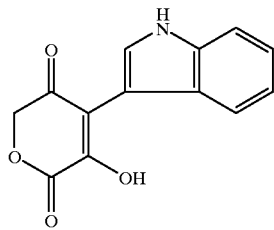

Step A: indole-3-acetyl chloride

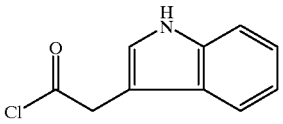

To a suspension of indole-3-acetic acid (1.0 g, 5.7 mmol) in $CH_2Cl_2$ at 0° C. was added DMF (20 μL), followed by oxalyl chloride (2.5 g, 20 mmol). The reaction mixture was stirred at 0° C. for 1.5 h. The solvent was removed in vacuo to give 1.25 g of the crude product, which was used in the next step without further purification.

Step B

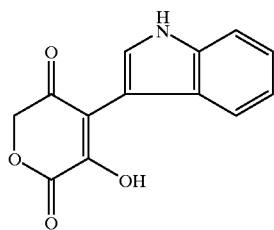

Prepared as described in Preparative Example 1 starting from indole-3-acetyl chloride obtained in the previous step.

¹H NMR (Acetone-d₆, 400 MHz) δ7.75 (s, 1H), 7.58 (d, 1H), 7.43 (d, 1H), 7.12 (t, 1H), 7.03 (t, 1H), 5.15 (s, 2H).

PREPARATIVE EXAMPLE 4

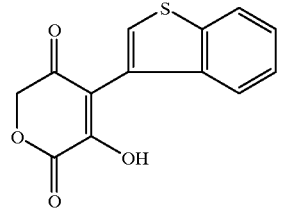

Using the procedure set forth in Preparative Example 1, and substituting benzo[b]thiophene-3-acetyl chloride for phenylacetyl chloride, the target compound was prepared.

¹H NMR (CDCl₃, 400 MHz) δ7.92 (m, 1H), 7.70 (s, 1H), 7.52 (m, 1H), 7.40 (m, overlapping signals, 2H), 5.20 (s, 2H).

Example 1

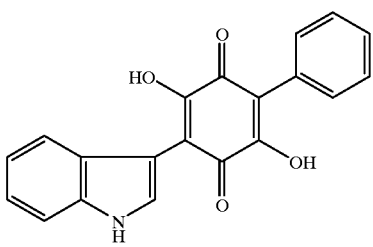

Step A

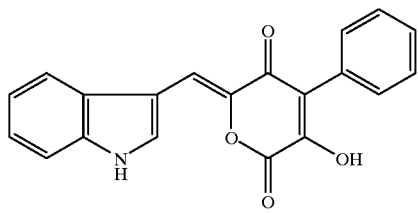

A mixture of the compound of Preparative Example 1 (560 mg, 2.74 mmol) and indole-3-carboxaldehyde (435 mg, 3.0 mmol) in acetic acid (7.5 mL) was heated at 60° C. until a clear solution was formed. To this solution was added 4 drops of concentrated HCl. The resultant reddish solution was heated at 90° C. for 3 h. After cooling to room temperature, the reaction was diluted with a 1:1 mixture of ether/hexanes (10 mL), then stirred at 0° C. for 10 min. The reddish crystalline product (890 mg) was collected by filtration.

¹H NMR (Acetone-d₆, 400 MHz) δ8.27 (d, 1H), 7.98 (m, 1H), 7.56 (m, 3H), 7.52 (s, 1H), 7.44 (m, 2H), 7.38 (tt, 1H), 7.26 (ddd, 1H), 7.23 (ddd, 1H).

Step B

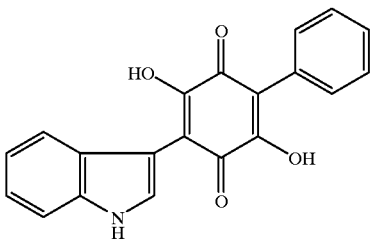

To a suspension of the intermediate from step A (710 mg, 2.14 mmol) in methanol at room temperature was added a solution of NaOMe in MeOH (25 wt %, 20 mL). The mixture was stirred for 2.5 h before it was poured slowly into an ice-cold 1.0 N HCl solution (120 mL). The precipitate was collected by filtration, washed thoroughly with water, and dried under high vacuum. Recrystallization from THF/hexanes gave 580 mg of the product as a greenish solid.

¹H NMR (Acetone-d₆, 400 MHz) δ7.65 (d, 1H), 7.59 (m, 1H), 7.55 (m, 2H), 7.43 (m, 3H), 7.35 (tt, 1H), 7.13 (ddd, 1H), 7.04 (ddd, 1H).

Example 2

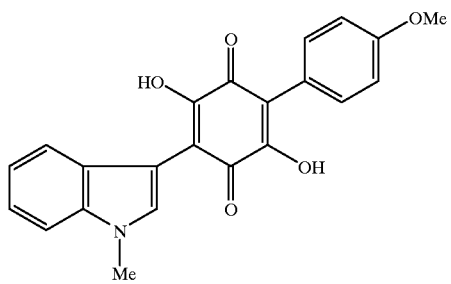

Using the procedure set forth in Example 1, and starting from the compound of preparative example 2 and 1-methylindole-3-carboxaldehyde the target compound was prepared.

¹H NMR (Acetone-d₆, 400 MHz) δ7.58 (dt, 1H), 7.54 (s, 1H), 7.51 (d, 2H), 7.42 (dt, 1H), 7.19 (ddd, 1H), 7.05 (ddd, 1H), 6.98 (d, 2H), 3.91 (s, 3H), 3.83 (s, 3H).

Example 3

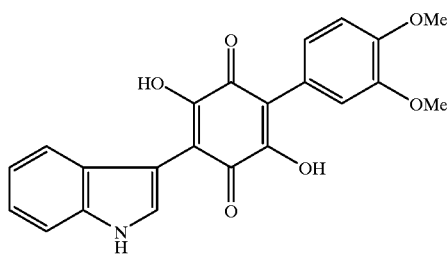

Step A

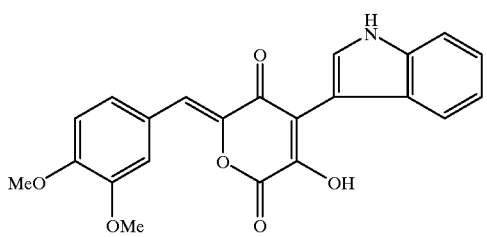

The compound of preparative example 3 (9.4 mg, 0.039 mmol) and 3,4-dimethoxybenzaldehyde (16 mg, 0.1 mmol) were dissolved in acetic acid (1.0 mL) at 60° C. and 1 drop of concentrated HCl was added. The reaction mixture was warmed to 90° C. where it was stirred for 3 h. After cooling to room temperature, the reaction was partitioned between EtOAc (20 mL) and water (10 mL). The organic layer was dried over anhydrous $MgSO_4$, filtered and concentrated in vacuo. The residue was purified by preparative TLC plates ($SiO_2$, EtOAc) to give 6.0 mg of the product.

$^1$H NMR (Acetone-$d_6$, 400 MHz) δ7.83 (d, 1H), 7.62 (m, 1H), 7.58 (m, 1H), 7.44 (t, 1H), 7.16–7.00 (m, 4H), 3.80 (s, 6H).

Step B

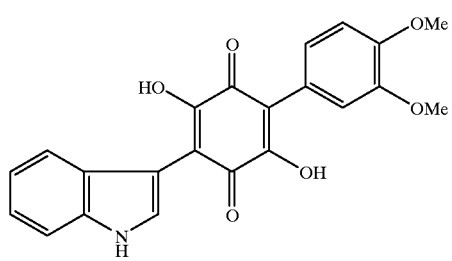

To a solution of the intermediate obtained from the previous step (5.5 mg) in methanol (1.0 mL) at room temperature was added a solution of NaOMe in methanol (25 wt %, 1.0 mL). After 3 h, the reaction mixture was poured into 1.0 N HCl solution (10 mL), extracted with EtOAc (15 mL). The extract was washed with water and brine, dried over anhydrous $MgSO_4$, filtered, and concentrated in vacuo. The residue was purified by HPLC to give 2.6 mg of the product.

$^1$H NMR ($CDCl_3$/Acetone-$d_6$, 400 MHz) δ7.50 (d, J=2.8 Hz, 1H), 7.46 (d, J=8.0 Hz, 1H), 7.27 (d, J=8.1 Hz, 1H), 7.08–6.95 (m, 4H), 6.81 (d, J=8.4 Hz, 1H), 3.78 (s, 3H), 3.76 (s, 3H).

Example 4

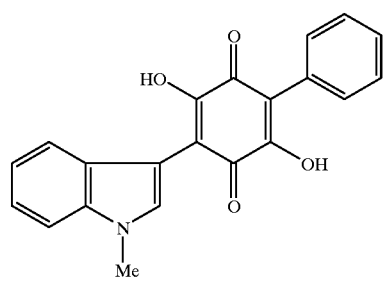

Using the procedure set forth in Example 1, and starting from the compound of Preparative Example 1 and 1-methylindole-3-carboxaldehyde, the target compound was prepared.

$^1$H NMR (Acetone-$d_6$, 400 MHz) δ7.6–7.5 (m, overlapping signals, 4H), 7.43 (m, overlapping signals, 3H), 7.36 (m, 1H), 7.19 (t, 1H), 7.06 (t, 1H), 3.91 (s, 3H).

Example 5

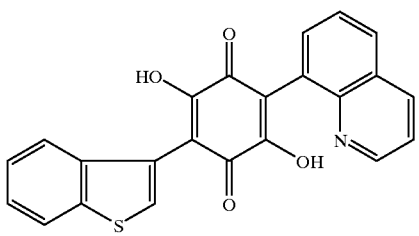

Using the procedure set forth in Example 1, and starting from the compound of Preparative Example 4 and 8-quinolinecarboxaldehyde, the target compound was prepared.

$^1$H NMR (DMSO-$d_6$, 400 MHz) δ8.89 (d, J=1.5 Hz, 1H), 8.53 (d, J=7.8 Hz, 1H), 8.05 (d, J=7.8 Hz, 1H), 8.00 (m, 1H), 7.52 (m, overlapping signals, 3H), 7.60 (m, overlapping signals, 2H), 7.36 (m, overlapping signals, 2H).

The procedures described in the examples noted above were used to prepare the compounds shown in Table I, using modified starting materials.

Utility for the compounds of formula I is demonstrated using the following assays.

Cell-based Assay for Insulin Receptor Tyrosine Phosphorylation

CHO.T cells, which overexpress human insulin receptor are cultured in Hams F12 medium supplemented with 10% fetal calf serum, fungizone, penicillin and streptomycin at approximately $1.5 \times 10^5$ cells/well. The 96-well plates are incubated for approximately 24 h at 37° C., which is when the cells reached confluency. The cells are washed with phosphate buffered saline (PBS) three times and then incubated in serum-free medium for 3 h at 37° C. Insulin and/or test compounds are added to the wells, and the cells are incubated for an additional 20 min at 37° C. The cells are washed three times with PBS and lysates are prepared. The lysates are transferred to a second 96 well plate. The wells of the second plate are precoated with monoclonal anti-insulin receptor antibody. Antibody is diluted to a final concentration of approximately 4 mcg/mL in 20 mM $NaHCO_3$, pH 9.6. Approximately 50 mcL of diluted antibody solution is added to each well. The lysates are incubated for 16 h at 4° C. to immunopurify the insulin receptor.

To detect the level of tyrosine phosphorylation of the insulin receptor captured on the plates, the washed plates are incubated for 5 h at 4° C. with monoclonal antiphosphotyrosine antibody conjugated to alkaline phosphatase (Transduction Laboratories). The unbound antibody is removed and chromogenic substrate of alkaline phosphotase is added to the wells. Signals are detected at 405 nm with a microtiter plate reader.

The cell culture conditions, preparation of lysates, and assays are essentially those described in B. Zhang et al., *J. Biol. Chem.*, Vol. 266, pages 990–996 (1991) and Zhang and Roth, *J. Biol. Chem.*, Vol. 267, pages 18320–18328, (1992). Cell-based Assay for Insulin Receptor Tyrosine Kinase Activity CHO.T cells (approximately 1.5×10⁵ cells/well) were cultured in Hams F12 medium supplemented with 10% fetal calf serum, fungizone, penicillin and streptomycin. The 96-well plates are incubated for approximately 24 h at 37° C., which is when the cells reached confluency. The cells are washed with phosphate buffered saline (PBS) three times and then incubated in serum-free medium for 3 h at 37° C. Insulin and/or test compounds are added to the wells, and the cells are incubated for an additional 20 min at 37° C. The cells are washed three times with PBS and lysates are prepared. The lysates are transferred to a second 96 well plate. The wells of the second plate are precoated with monoclonal anti-insulin receptor antibody. Antibody is diluted to a final concentration of approximately 4 mcg/mL in 20 mM NaHCO₃, pH 9.6. Approximately 150 mcL of diluted antibody solution is added to each well. The lysates are incubated for 16 h at 4° C. to immunopurify the insulin receptor.

To determine the insulin receptor tyrosine kinase activity, twenty microliters of the kinase reaction mixture (50 mM Hepes, pH 7.6, 150 mM NaCl, 5 mM MgCl₂, 5 mM MnCl₂, 0.1% Triton X-100, 1 mg/ml poly(Glu:Tyr)(4:1), 2 m Ci of carrier-free [g-³²P]ATP) is added to each well of the 96-well plates and the incubation is continued at 25° C. for 40 min. The reaction is terminated by addition of 50 ml 100 mM phosphoric acid. The mixture is transferred to Multiscreen PH plates and washed. The radioactivities associated with the wells are determined using a Topcount. The insulin receptor tyrosine kinase activities stimulated by test agents are compared to that stimulated by insulin.

In Vitro Assay for Insulin Receptor Tyrosine Kinase Activity

A glutathione S-transferase fusion protein containing intracellular domain of the insulin receptor (GST-IRTK) was expressed in Baculovirus and affinity purified using glutathione-conjugated sepharose. To activated the insulin receptor tyrosine kinase, an aliquot of the GST-IRTK (200 nM final concentration) was incubated at 25 C. for 15 min in a buffer containing 50 mM Tris-HCl (pH 7.4), 8 mM MgCl₂, and varying concentrations of ATP (from 1 μM to 1 mM) in the absence or presence of test compounds. A substrate protein (histone H2B) (0.35 μg/μl final concentration) was then added and the incubation was continued at 25 C. for 15 min and terminated by the addition of 50 mM EDTA. The reaction mixtures were separated by SDS-PAGE followed by immunoblotting. The blots were probed with a monoclonal anti-phosphotyrosine antibody and developed using the ECF reagents. The level of tyrosine phosphorylation of GST-IRTK and histone H2B was determined using image analyses. Alternatively, following activation of GST-IRTK with ATP in the presence or absence of test compounds, histone H2B and 32-γ-ATP were added to the reaction mixtures. The samples were analyzed by SDS-PAGE followed by autoradiography.

In Vivo Assay for Oral Anti-hyperglycemic Activity

Genetically altered obese diabetic mice (db/db) (male, 7–9 weeks old) are housed (7–9 mice/cage) under standard laboratory conditions at 22° C. and 50% relative humidity, and maintained on a diet of Purina rodent chow and water ad libitum. Prior to treatment, blood is collected from the tail vein of each animal and blood glucose concentrations are determined using One Touch BasicGlucose Monitor System (Lifescan). Mice that have plasma glucose levels between 250 to 500 mg/dl are used. Each treatment group consists of seven mice that are distributed so that the mean glucose levels are equivalent in each group at the start of the study. db/db mice are dosed orally by gavage with either vehicle (containing 0.5% methylcellulose ) or test compound from 0.2 to 30 mg/kg in a volume of 10 ml/kg. Blood is sampled from the tail vein hourly for 4 hours and at 24, 30 h post-dosing and analyzed for blood glucose concentrations. Food is withdrawn from 0–4 h post dosing and reintroduced thereafter. Individual body weights and mean food consumption (each cage) are also measured after 24 h. Significant differences between groups (comparing drug-treated to vehicle-treated) are evaluated using Student t-test.

While certain preferred embodiments are described in detail, numerous alternative embodiments are contemplated as falling within the invention. Consequently, the claims are not to be limited to the specific teachings herein.

What is claimed is:

1. A compound represented by formula I:

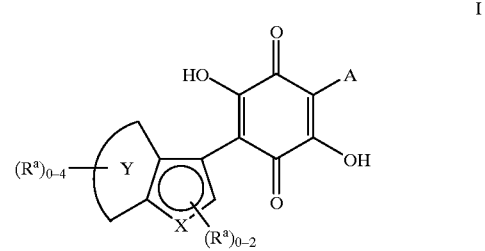

or a tautomer, salt, hydrate, prodrug or reduced form thereof wherein:

ring Y represents a 5–6 membered aryl or heteroaryl fused ring, which is optionally substituted with 1–4 groups selected from $R^a$;

X represents O, $S(O)_m$ or N, wherein m is 0, 1 or 2;

A represents a member selected from the group consisting of:
(a) a 6–10 membered mono-or bicyclic aryl group;
(b) a 5–6 membered isolated monocyclic heteroaryl group;
(c) a 9–10 membered bicyclic heteroaryl group, attachment to which is through a 6 membered ring, or
(d) an 8-membered bicyclic heteroaryl group, the heteroaryl groups having 1–4 heteroatoms selected from O, $S(O)_m$ and N, said aryl and heteroaryl groups being optionally substituted with 1–3 $R^a$ groups;

each $R^a$ is independently selected from the group consisting of:
halo, —OH, —$C_{1-12}$ alkyl($R^b$)₃, —$C_{2-10}$ alkenyl($R^b$)₃, —$C_{2-10}$ alkynyl($R^b$)₃, —$C_{6-10}$ aryl($R^b$)₃, -heteroaryl($R^b$)₃, -heterocyclyl($R^b$)₃, —NH₂, —NHC₁₋₆ alkyl($R^b$)₃, —N(C₁₋₆ alkyl($R^b$)₃)₂, —N₃, —OC₁₋₆ alkyl($R^b$)₃, —$S(O)_m$H, —$S(O)_m$C₁₋₆ alkyl($R^b$)₃, —CHO, —C(O)C₁₋₆ alkyl($R^b$)₃, —CO₂H, —C(O)OC₁₋₆ alkyl($R^b$)₃, —C(O)SC₁₋₆ alkyl($R^b$)₃, —C(O)NH₂, —C(O)NHC₁₋₆ alkyl($R^b$)₃, —NHC(O)C₁₋₆ alkyl($R^b$)₃, —$S(O)_m$NH₂, —NHS(O)$_m$C₁₋₆ alkyl($R^b$)₃, —$S(O)_m$NHC₁₋₆ alkyl($R^b$)₃ and —$S(O)_m$N(C₁₋₆ alkyl($R^b$)₃)₂, and each $R^b$ is independently selected from: H, OH, halo, —C₁₋₄ alkyl, —C₂₋₄ alkenyl, —C₂₋₄ alkynyl, —CF₃, —OCF₃, —NO₂, —N₃, —CHO, —OC₁₋₆ alkyl, —$S(O)_m$C₁₋₆ alkyl, —NH₂, —NHC₁₋₆ alkyl, —N(C₁₋₆ alkyl)₂, —C(O)C₁₋₆ alkyl, —CO₂H, —CO₂C₁₋₆ alkyl, —C(O)NH₂, —C(O)NHC₁₋₆ alkyl, —C(O)N(C₁₋₆ alkyl)₂, —OC(O)C₁₋₆ alkyl, —NHC(O)C₁₋₆ alkyl, —$S(O)_m$NH₂, —$S(O)_m$NHC₁₋₆ alkyl, —$S(O)_m$(C₁₋₆ alkyl)₂, aryl, heteroaryl and heterocyclyl.

2. A compound in accordance with claim 1 wherein:

represents a phenyl ring.

3. A compound in accordance with claim 1 wherein:

represents a pyrrole ring.

4. A compound in accordance with claim 1 wherein:

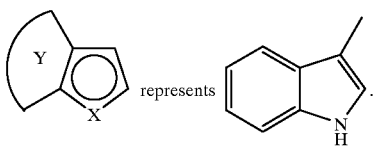

5. A compound in accordance with claim 1 wherein:
1–4 $R^a$ groups are present, and each $R^a$ is independently selected from the group consisting of:
halo, —OH, —$C_{1-12}$ alkyl($R^b$)$_3$, —$C_{2-10}$ alkenyl($R^b$)$_3$, —$C_{2-10}$ alkynyl($R^b$)$_3$, —$C_{6-10}$ aryl($R^b$)$_3$,-heteroaryl ($R^b$)$_3$,-heterocyclyl($R^b$)$_3$, —NH$_2$, —NHC$_{1-6}$ alkyl ($R^b$)$_3$, —N(C$_{1-6}$ alkyl($R^b$)$_3$)$_2$, —N$_3$, —OC$_{1-6}$ alkyl ($R^b$)$_3$, —S(O)$_m$H, —S(O)$_m$C$_{1-6}$ alkyl($R^b$)$_3$, —CHO, —C(O)C$_{1-6}$ alkyl($R^b$)$_3$, —CO$_2$H, —C(O)OC$_{1-6}$ alkyl($R^b$)$_3$, —C(O)SC$_{1-6}$ alkyl($R^b$)$_3$, —C(O)NH$_2$, —C(O)NHC$_{1-6}$ alkyl($R^b$)$_3$, —NHC(O)C$_{1-6}$ alkyl ($R^b$)$_3$, —S(O)$_m$NH$_2$, —NHS(O)$_m$C$_{1-6}$ alkyl($R^b$)$_3$, —S(O)$_m$NHC$_{1-6}$ alkyl($R^b$)$_3$ and —S(O)$_m$N(C$_{l-6}$ alkyl($R^b$)$_3$)$_2$,
and each $R^b$ is independently selected from: H, OH, halo, —C$_{1-4}$ alkyl, —C$_{2-4}$ alkenyl, —C$_{2-4}$ alkynyl, —CF$_3$, —OCF$_3$, —NO$_2$, —N$_3$, —CHO, —OC$_{1-6}$ alkyl, —S(O)$_m$C$_{1-6}$ alkyl, —NH$_2$, —NHC$_{1-6}$ alkyl, —N(C$_{1-6}$ alkyl)$_2$, —C(O)C$_{l-6}$ alkyl, —CO$_2$H, —CO$_2$C$_{1-6}$ alkyl, —C(O)NH$_2$, —C(O)NHC$_{1-6}$ alkyl, —C(O)N(C$_{1-6}$ alkyl)$_2$, —OC(O)C$_{1-6}$ alkyl, —NHC(O)C$_{1-6}$ alkyl, —S(O)$_m$NH$_2$, —S(O)$_m$NHC$_{1-6}$ alkyl, —S(O)$_m$(C$_{1-6}$ alkyl)$_2$, aryl, heteroaryl and heterocyclyl.

6. A compound in accordance with claim 1 wherein:
A represents a member selected from the group consisting of:
a 6–10 membered mono-or bicyclic aryl group or
a 9–10 membered bicyclic heteroaryl group, attachment to which is through a 6 membered ring, the heteroaryl groups having 1–4 heteroatoms selected from O, S(O)$_m$ and N,
said aryl and heteroaryl groups being optionally substituted with 1–3 $R^a$ groups.

7. A compound in accordance with claim 1 wherein:
A represents an aryl group selected from phenyl and naphthyl, optionally substituted with 1–3 $R^a$ groups.

8. A compound in accordance with claim 1 wherein:
A represents a 9–10 membered bicyclic heteroaryl group, attachment to which is through a 6 membered ring, said heteroaryl group having 1–4 heteroatoms selected from O, S(O)$_m$ and N, and being optionally substituted with 1–3 $R^a$ groups.

9. A compound in accordance with claim 1 wherein:
A represents a 9–10 membered bicyclic heteroaryl group selected from the group consisting of:

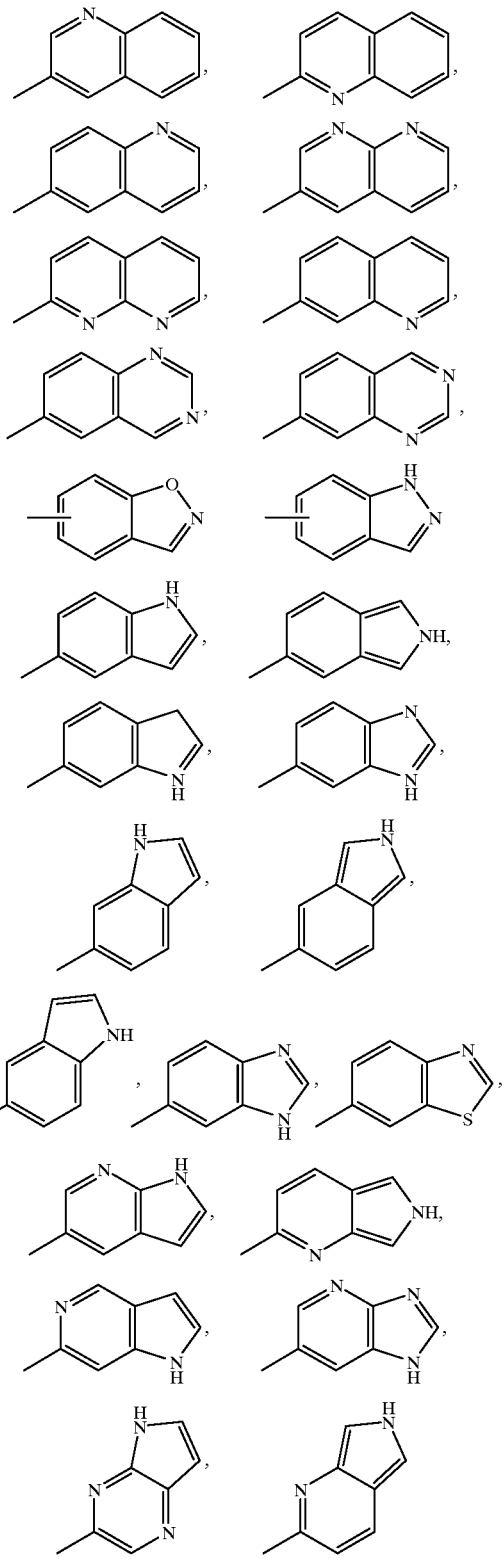

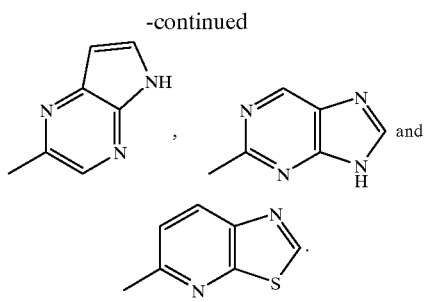

10. A compound in accordance with claim 1 wherein:
A represents a 5–6 membered isolated monocyclic heteroaryl group, having 1–3 heteroatoms selected from O, S(O)$_m$ and N, optionally substituted with 1–3 R$^a$ groups.

11. A compound in accordance with claim 10 wherein A is selected from the group consisting of: pyrrole, imidazole, triazole, pyridine, pyrimidine, pyrazine, furan, thiophene, oxazole and thiazole.

12. A compound in accordance with claim 1 wherein the moiety:

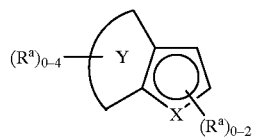

has 1–4 R$^a$ groups attached, said R$^a$ groups being selected from the group consisting of:
halo, —C$_{1-12}$ alkyl(R$^b$)$_3$, —NH$_2$, —NHC$_{1-6}$ alkyl(R$^b$)$_3$, —N(C$_{1-6}$ alkyl(R$^b$)$_3$)$_2$, —N$_3$, —OC$_{1-6}$ alkyl(R$^b$)$_3$, —S(O)$_m$H, —S(O)$_m$C$_{1-6}$ alkyl(R$^b$)$_3$, —C(O)C$_{1-6}$ alkyl(R$^b$)$_3$, —CO$_2$H, —C(O)OC$_{1-6}$ alkyl(R$^b$)$_3$, —C(O)NH$_2$, —C(O)NHC$_{1-6}$ alkyl(R$^b$)$_3$, —NHC(O)C$_{1-6}$ alkyl(R$^b$)$_3$, —S(O)$_m$NH$_2$, —NHS(O)$_m$C$_{1-6}$ alkyl(R$^b$)$_3$, —S(O)$_m$NHC$_{1-6}$ alkyl(R$^b$)$_3$ and —S(O)$_m$N(C$_{1-6}$ alkyl(R$^b$)$_3$)$_2$, and each R$^b$ is independently selected from: H, OH, halo, —CF$_3$, —OCF$_3$, —NO$_2$, —N$_3$, —OC$_{1-6}$ alkyl, —S(O)$_m$C$_{1-6}$ alkyl, —NH$_2$, —NHC$_{1-6}$ alkyl, —N(C$_{1-6}$ alkyl)$_2$, —C(O)C$_{1-6}$ alkyl, —CO$_2$H, —CO$_2$C$_{1-6}$ alkyl, —C(O)NH$_2$, —C(O)NHC$_{1-6}$ alkyl, —C(O)N(C$_{1-6}$ alkyl)$_2$, —NHC(O)C$_{1-6}$ alkyl, —S(O)$_m$NH$_2$, —S(O)$_m$NHC$_{1-6}$ alkyl, —S(O)$_m$(C$_{1-6}$ alkyl)$_2$, aryl, heteroaryl and heterocyclyl.

13. A compound in accordance with claim 1 wherein:
A represents a phenyl ring, unsubstituted or substituted with 1–3 R$^a$ moieties selected from the group consisting of:
halo, —C$_{1-12}$ alkyl(R$^b$)$_3$, —NH$_2$, —NHC$_{1-6}$ alkyl(R$^b$)$_3$, —N(C$_{1-6}$ alkyl(R$^b$)$_3$)$_2$, —N$_3$, —OC$_{1-6}$ alkyl(R$^b$)$_3$, —S(O)$_m$H, —S(O)$_m$C$_{1-6}$ alkyl(R$^b$)$_3$, —C(O)C$_{1-6}$ alkyl(R$^b$)$_3$, —CO$_2$H, —C(O)OC$_{1-6}$ alkyl(R$^b$)$_3$, —C(O)NH$_2$, —C(O)NHC$_{1-6}$ alkyl(R$^b$)$_3$, —NHC(O)C$_{1-6}$ alkyl(R$^b$)$_3$, —S(O)$_m$NH$_2$, —NHS(O)$_m$C$_{1-6}$ alkyl(R$^b$)$_3$, —S(O)$_m$NHC$_{1-6}$ alkyl(R$^b$)$_3$ and —S(O)$_m$N(C$_{1-6}$ alkyl(R$^b$)$_3$)$_2$, and each R$^b$ is independently selected from: H, OH, halo, —CF$_3$, —OCF$_3$, —NO$_2$, —N$_3$, —OC$_{1-6}$ alkyl, —S(O)$_m$C$_{1-6}$ alkyl, —NH$_2$, —NHC$_{1-6}$ alkyl, —N(C$_{1-6}$ alkyl)$_2$, —C(O)C$_{1-6}$ alkyl, —CO$_2$H, —CO$_2$C$_{1-6}$ alkyl, —C(O)NH$_2$, —C(O)NHC$_{1-6}$ alkyl, —C(O)N(C$_{1-6}$ alkyl)$_2$, —NHC(O)C$_{1-6}$ alkyl, —S(O)$_m$NH$_2$, —S(O)$_m$NHC$_{1-6}$ alkyl, —S(O)$_m$(C$_{1-6}$ alkyl)$_2$, aryl, heteroaryl and heterocyclyl.

14. A compound in accordance with claim 1 of formula Ia:

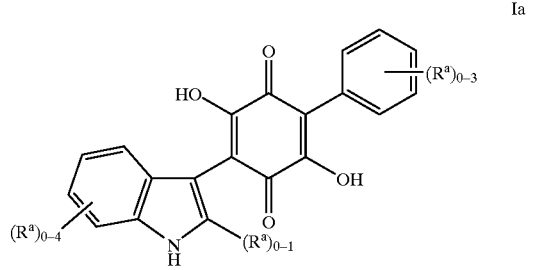

wherein R$^a$ is as originally defined.

15. A compound in accordance with claim I of the formula Ib:

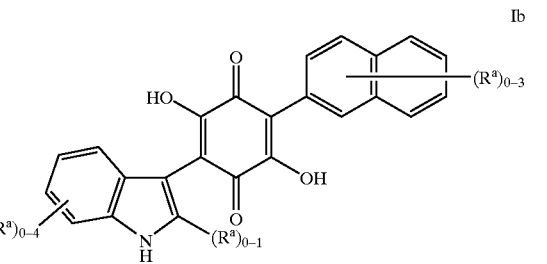

wherein R$^a$ is as originally defined.

16. A compound in accordance with claim 14 wherein:
0–3 R$^a$ groups are present in the molecule and are selected from the group consisting of: halo, —C$_{1-12}$ alkyl(R$^b$)$_3$, —NH$_2$, —NHC$_{1-6}$ alkyl(R$^b$)$_3$, —N(C$_{1-6}$ alkyl(R$^b$)$_3$)$_2$, —N$_3$, —OC$_{1-6}$ alkyl(R$^b$)$_3$, —S(O)$_m$H, —S(O)$_m$C$_{1-6}$ alkyl(R$^b$)$_3$, —C(O)C$_{1-6}$ alkyl(R$^b$)$_3$, —CO$_2$H, —C(O)OC$_{1-6}$ alkyl(R$^b$)$_3$, —C(O)NH$_2$, —C(O)NHC$_{1-6}$ alkyl(R$^b$)$_3$, —NHC(O)C$_{1-6}$ alkyl(R$^b$)$_3$, —S(O)$_m$NH$_2$, —NHS(O)$_m$C$_{1-6}$ alkyl(R$^b$)$_3$, —S(O)$_m$NHC$_{1-6}$ alkyl(R$^b$)$_3$ and —S(O)$_m$N(C$_{1-6}$ alkyl(R$^b$)$_3$)$_2$, and each R$^b$ is independently selected from: H, OH, halo, —CF$_3$, —OCF$_3$, —NO$_2$, —N$_3$, —OC$_{1-6}$ alkyl, —S(O)$_m$C$_{1-6}$ alkyl, —NH$_2$, —NHC$_{1-6}$ alkyl, —N(C$_{1-6}$ alkyl)$_2$, —C(O)C$_{1-6}$ alkyl, —CO$_2$H, —CO$_2$C$_{1-6}$ alkyl, —C(O)NH$_2$, —C(O)NHC$_{1-6}$ alkyl, —C(O)N(C$_{1-6}$ alkyl)$_2$, —NHC(O)C$_{1-6}$ alkyl, —S(O)$_m$NH$_2$, —S(O)$_m$NHC$_{1-6}$ alkyl, —S(O)$_m$(C$_{1-6}$ alkyl)$_2$, aryl, heteroaryl and heterocyclyl, and m is 0, 1 or 2.

17. A compound in accordance with claim 15 wherein:
0–3 R$^a$ groups are present in the molecule and are selected from the group consisting of: halo, —C$_{1-12}$ alkyl(R$^b$)$_3$, —NH$_2$, —NHC$_{1-6}$ alkyl(R$^b$)$_3$, —N(C$_{1-6}$ alkyl(R$^b$)$_3$)$_2$, —N$_3$, —OC$_{1-6}$ alkyl(R$^b$)$_3$, —S(O)$_m$H, —S(O)$_m$C$_{1-6}$ alkyl(R$^b$)$_3$, —C(O)C$_{1-6}$ alkyl(R$^b$)$_3$, —CO$_2$H, —C(O)OC$_{1-6}$ alkyl(R$^b$)$_3$, —C(O)NH$_2$, —C(O)NHC$_{1-6}$ alkyl(R$^b$)$_3$, —NHC(O)C$_{1-6}$ alkyl(R$^b$)$_3$, —S(O)$_m$NH$_2$, —NHS(O)$_m$C$_{1-6}$ alkyl(R$^b$)$_3$, —S(O)$_m$NHC$_{1-6}$ alkyl(R$^b$)$_3$ and —S(O)$_m$N(C$_{1-6}$ alkyl(R$^b$)$_3$)$_2$, and each R$^b$ is independently selected from: H, OH, halo, —CF$_3$, —OCF$_3$, —NO$_2$, —N$_3$, —OC$_{1-6}$ alkyl, —S(O)$_m$C$_{1-6}$ alkyl, —NH$_2$, —NHC$_{1-6}$ alkyl, —N(C$_{1-6}$ alkyl)$_2$, —C(O)C$_{1-6}$ alkyl, —CO$_2$H, —CO$_2$C$_{1-6}$ alkyl, —C(O)NH$_2$, —C(O)NHC$_{1-6}$ alkyl, —C(O)N(C$_{1-6}$ alkyl)$_2$, —NHC(O)C$_{1-6}$ alkyl, —S(O)$_m$NH$_2$, —S(O)$_m$NHC$_{1-6}$ alkyl, —S(O)$_m$(C$_{1-6}$ alkyl)$_2$, aryl, heteroaryl and heterocyclyl, and m is 0, 1 or 2.
18. A compound in accordance with claim 1 selected from Table I:
TABLE I
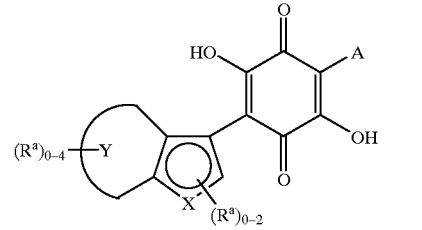
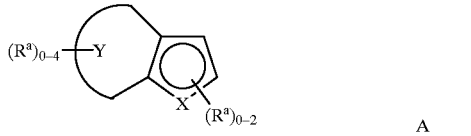
| | A |
|---|---|
| 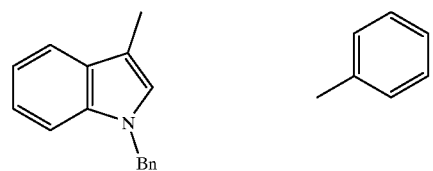 | |
TABLE I-continued
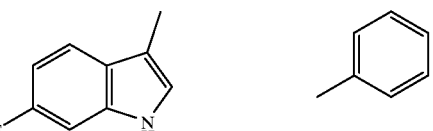
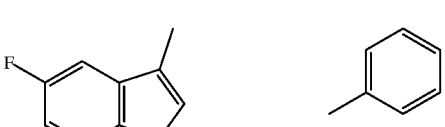
| | A |
|---|---|
|  | |
|  | |
| 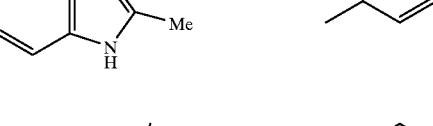 | |
|  | |

TABLE I-continued

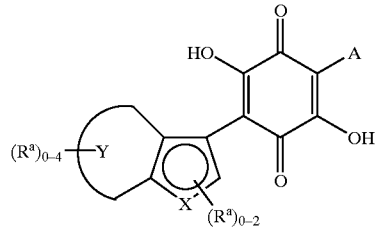

19. A pharmaceutical composition which is comprised of a compound as described in claim 1 in combination with a pharmaceutically acceptable carrier.

20. A method of treating or preventing diabetes in a mammalian patient in need thereof, which is comprised of administering to said patient a compound as described in claim 1 in an amount which is effective for treating or preventing diabetes.

21. A method of controlling blood glucose, triglyceride or fatty acid levels in a mammalian patient in need thereof, which is comprised of administering to said patient a compound as described in claim 1 in an amount which is effective for controlling blood glucose, triglyceride or fatty acid levels.

22. A method of treating a mammalian patient for obesity, which is comprised of administering to said patient a compound as described in claim 1 in an amount which is effective for treating obesity.

23. A method of treating or preventing diabetes or obesity comprising administering to a mammalian patient in need thereof, a compound as described in claim I and a member selected from the group consisting of:

insulin, a sulfonylurea, a biguanide, an α-glucosidase inhibitor, a peroxisome proliferator-activater receptor γ agonist, a cholesterol lowering agent, a bile acid sequestrant, a nicotinyl alcohol or nicotinic acid, a peroxisome proliferator-activater receptor α agonist and probucol.

24. A compound in accordance with claim 1 and represented by the formula:

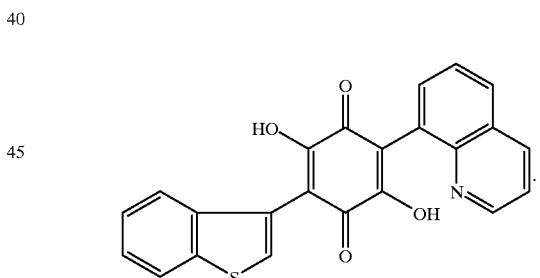

* * * * *